United States Patent

Appleton et al.

Patent Number: 5,387,597
Date of Patent: Feb. 7, 1995

[54] HEMIPHOSPHATE HEMIHYDRATE OF 2-(1-PENTYL-3-GUANIDINO)-4-(2-METHYL-4-IMIDAZOLYL)THIAZOLE

[75] Inventors: Troy A. Appleton; Ward M. Smith, both of Mystic, Conn.

[73] Assignee: Pfizer Inc., New York, N.Y.

[21] Appl. No.: 900,973

[22] Filed: Jun. 18, 1992

Related U.S. Application Data

[63] Continuation-in-part of Ser. No. 656,162, Feb. 25, 1991, abandoned.

[51] Int. Cl.6 .................. C07D 417/04; A61K 31/425
[52] U.S. Cl. .................... 514/370; 548/198
[58] Field of Search .................. 548/198; 514/370

[56] References Cited

U.S. PATENT DOCUMENTS

| | | | |
|---|---|---|---|
| 4,560,690 | 12/1985 | Reiter | 514/256 |
| 4,997,949 | 3/1991 | Allen et al. | 548/198 |
| 4,997,981 | 3/1991 | Hill et al. | 564/30 |

*Primary Examiner*—Robert Gerstl
*Attorney, Agent, or Firm*—Peter C. Richardson; Gregg C. Benson; Robert T. Ronau

[57] ABSTRACT

The hemiphosphate hemihydrate salt of 2-(1-pentyl-3-guanidino)-4-(2-methyl-4-imidazolyl)thiazole is the preferred salt of this antiulcer agent.

2 Claims, No Drawings

HEMIPHOSPHATE HEMIHYDRATE OF 2-(1-PENTYL-3-GUANIDINO)-4-(2-METHYL-4-IMIDAZOLYL)THIAZOLE

This application is a continuation-in-part of application Ser. No. 07/656,162, filed Feb. 25, 1991, now abandoned.

BACKGROUND OF THE INVENTION

The present invention is directed to a hemiphosphate hemihydrate salt of 2-(1-pentyl-3-guanidino)-4-(2-methyl-4-imidazolyl)thiazole having advantageous properties.

U.S. Pat. No. 4,560,690 which is herein incorporated by reference, describes 2-(1-pentyl-3-guanidino)-4-(2-methyl-4-imidazolyl)thiazole and analogs as having antiulcer activity. The form of this preferred compound, reported in said patent is the anhydrous dihydrobromide salt, which is noncrystalline, difficult to purify and possesses properties which are generally less suitable for formulation and use as a medicinal agent in mammals.

International Application No. PCT/US86/02308 (now U.S. Pat. No. 4,997,981), herein incorporated by reference, reports a further improvement in salts of this preferred antiulcer agent and describes the preparation and properties of the dihydrochloride trihydrate salt.

Formulations are generally required in the administration of medicinal agents for a variety of reasons, including taste improvement, accurate delivery, safety (i.e. protection of non-targeted organs and the facilitation of the manufacture of the dosage forms. In the preparation of a dosage form, therefore, various excipients are added to obtain a dosage form that is suitable for administration. When the administration route is to be oral, it is often desirable to add sweeteners, flavorants, taste-maskers, binders, plasticizers, lubricants, swelling matrices, disintegrants, wetting agents and the like. These excipients facilitate manufacture and help to improve patient compliance.

Patient compliance is an important factor in the self-administration of orally-administered medicinal agents, and can be low when the patient is requested to self-administer multiple tablets, overlarge tablets or tablets which exhibit disagreeable flavor characteristics. Many patients experience either psychological (e.g., anxiety) or physiological (e.g., gag reflex) problems when attempting to self-administer medicinal agents. Thus it can be of great benefit to reduce the number of tablets necessary and to reduce the size of said tablets in an effort to improve patient compliance.

Therefore it is necessary to minimize the amount of excipients utilized to keep the dosage size small. The amounts of the various excipients used are therefore limited by the size of the dosage form and by the amount of drug substance in the dosage form. As the dose of the drug increases, the formulator is allowed less excipient with which to modify the properties of the drug powder. Once the drug powder dominates the dosage form at concentrations above 50%, the excipients may become less effective. This could necessitate the division of the dose into two or more tablets or capsules, which as mentioned hereinabove is not pharmacologically desirable. An attractive alternative to dividing the dose in such a manner is to increase the potency of the active ingredient. Increased potency can be achieved by reducing the molecular weight of the active agent being used thereby resulting in a lower mass of active agent being necessary to achieve the desired activity. When high molecular weight salts are utilized in the preparation of the formulation, as is often necessary to achieve the proper characteristics of stability and crystallinity, the potency can be improved by the substitution of lower molecular weight salt forms.

It is the object of this invention, therefore, to provide a more potent form of 2-(1-pentyl-3-guanidino)-4-(2-methyl-4-imidazolyl)thiazole, namely the hemiphosphate hemihydrate salt thereof.

SUMMARY OF THE INVENTION

It has now been found that a yet unreported salt of 2-(1-pentyl-3-guanidino)-4-(2-methyl-4-imidazolyl)thiazole, namely, the hemiphosphate hemihydrate, offers many advantages especially a high weight percent of active agent.

The present invention is also directed to a method of treating ulcers in a mammal suffering from ulcers comprising administering a single dose of 2-(1-pentyl-3-guanidino)-4-(2-methyl-4-imidazolyl)thiazole.

DETAILED DESCRIPTION OF THE INVENTION 2-(1-Pentyl-3-guanidino)-4-(2-methyl-4-imidazolyl)thiazole hemiphosphate hemihydrate is prepared by solubilizing the dihydrochloride trihydrate salt (10 mg free base equivalent) per ml in a Ph 6.6, 0.2M Phosphate buffer containing acetone in the ratio one part (weight) acetone to four parts (weight) buffer. After standing overnight at room temperature, the desired product is removed by filtration and dried under vacuum at room temperature.

This hemiphosphate hemihydrate salt has all the characteristics desired in a drug to be formulated for human use; it is crystalline, stable, non-hygroscopic and contains a high weight percent of active agent. This latter characteristic is especially important in allowing the formulation of smaller tablets, capsules, etc., for oral administration. This can readily be seen from the following comparison of the various reported forms of 2-(1-pentyl-3-guanidino)-4-(2-methyl-4-imidazolyl)thiazole:

| FORM | MOLECULAR FORM | MOLECULAR WT. (GR/MOLE) | % POTENCY[1] |
|---|---|---|---|
| free base | $C_{13}H_{20}N_6S_1$ | 292.4 | 100% |
| dihydrochloride trihydrate | $C_{13}H_{20}N_6S_1$ 2HCl 3H$_2$O | 419.4 | 292.4/419.4 69.7% |
| hemiphosphate hemihydrate | $C_{13}H_{20}N_6S_1$ ½H$_3$PO$_4$ ½H$_2$O | 350.4 | 292.4/350.4 83.4% |

[1]Potency is defined as the ratio of the molecular weights of the free base to the salt form.

The following example is given by way of illustration and is not to be construed as a limitation of this invention.

EXAMPLE 1

2-(1-Pentyl-3-guanidino)-4-(2-methyl-4-imidazolyl)thiazole Hemiphosphate Hemihydrate Salt Sufficient 2-(1-pentyl-3-guanidino)-4-(2-methyl-4-imidazolyl)thiazole was added to 100 ml of a solution consisting, by weight, of 1 part acetone and 4 parts of a 0.2 H phosphate buffer to give a drug concentration of 10 mg free base equivalent/ml. The mixture was stirred until all the solids had dissolved and was then allowed to remain undisturbed at room temperature overnight. The precipitated crystals were filtered and dried at room temperature in vacuo for 24 hours.

The DSC data gathered on this material shows it to possess two low temperature endotherms and one high temperature endotherm associated with melting.

The TGA data shows a loss of approximately 3% of the total weight when heated to 170° C. This weight loss is likely due to water loss, since Karl Fischer readings show 3.2% water on the material.

Samples of the hemiphosphate hemihydrate were submitted for elemental analysis. The amount of carbon, hydrogen and nitrogen are within 3% of the theoretical value whereas phosphorous is slightly higher than the theoretical value. The titratable water is slightly higher than the theoretical water content for a hemihydrate (2.6%). The slightly higher % water could be accounted for by the presence of some surface water on the bulk.

The habit of the hemiphosphate hemihydrate crystals is more rod-like or bladed in character than the needle crystalline habit of the dihydrochloride trihydrate form. Single crystal studies showed that there are 8 molecules per unit cell. The single crystal data confirms that this is the hemiphosphate hemihydrate. X-ray powder diffraction patterns generated for the new form and for the dihydrochloride trihydrate form also verifies that these are two completely different forms.

Samples of the hemiphosphate hemihydrate were stored at 50° C. After 55 days, TGA data still shows a weight loss of 2.7% up to 170° C. and microscopically shows birefringence indicating that the form is physically stable under these conditions.

A tabulation of this information is as follows:

SOME PHYSICOCHEMICAL PROPERTIES OF 2-(1-PENTYL-3-GUANIDINO-4-(2-METHYL-4-IMIDAZOLYL)THIAZOLE HEMIPHOSPHATE HEMIHYDRATE

1. Thermal Properties

| | |
|---|---|
| Melting Point °C. (Onset of endothermic peak, DSC heating rate = 10° C./min) | 214° C. |
| Heating of Fusion (kcal/M) | 4.1 kcal/$\underline{M}$ |
| Percent weight loss (TGA heating rate = 10° C./min) to 170° C. | 2.9 (103°–169° C.) |

2. X-ray and Microscopic Analysis

| | |
|---|---|
| Single Crystal | crystalline, consistent with proposed composition |
| Powder Diffraction | crystalline |
| Microscopic Crystallinity | birefringent |

3. Elemental Analysis (Lot #16362-120-1)

| Element | Theoretical % ($\frac{1}{2}H_3PO_4$ $\frac{1}{2}H_2O$) | Actual % |
|---|---|---|
| C | 44.6 | 44.23 |
| H | 6.5 | 6.48 |
| N | 24.0 | 23.67 |
| P | 4.4 | 4.79 |
| $H_2O$ | 2.6 | 3.2(KF) |

4. Physical Stability after Storage at 50° C. (55 days)

| | |
|---|---|
| Percent Weight Loss (TGA) to 170° C. | 2.7% |
| Microscopic Crystallinity | birefringent |

We claim:

1. 2-(1-pentyl-3-guanidino)-4-(2-methyl-4-imidazolyl)thiazolehemiphosphate hemihydrate.

2. A method of treating ulcers in a mammal suffering from ulcers comprising administering a single dose of the compound according to claim 1.

* * * * *